United States Patent [19]

Lindel et al.

[11] Patent Number: 5,010,091
[45] Date of Patent: Apr. 23, 1991

[54] 2,4-DIHALOGENO-6-PYRIDYLETHANOL-PHENYLISOPROPYLAMINES FOR SHIFTING THE PROTEIN-FAT RATIO OF ANIMALS IN FAVOR OF PROTEIN

[75] Inventors: Hans Lindel, Leverkusen; Werner Hallenbach, Monheim; Friedrich Berschauer, Wuppertal; Heinrich Greife, Langenfeld; Gernot Klotz, Leichlingen, all of Fed. Rep. of Germany

[73] Assignee: Bayer Aktiengesellschaft, Leverkusen, Fed. Rep. of Germany

[21] Appl. No.: 477,272

[22] Filed: Feb. 8, 1990

[30] Foreign Application Priority Data

Feb. 18, 1989 [DE] Fed. Rep. of Germany ....... 3905028

[51] Int. Cl.$^5$ ................. C07D 213/61; C07D 213/89; A61K 31/44
[52] U.S. Cl. .................... 514/357; 546/334; 546/335; 546/336
[58] Field of Search ....... 546/334, 335, 336; 514/357

[56] References Cited

FOREIGN PATENT DOCUMENTS 0170538  5/1986  European Pat. Off. ............ 546/334
0254856  2/1988  European Pat. Off. ............ 546/334
0256420  2/1988  European Pat. Off. ............ 546/334

Primary Examiner—Frederick E. Waddell
Assistant Examiner—Zinna Northington-Davis
Attorney, Agent, or Firm—Sprung Horn Kramer & Woods

[57] ABSTRACT 2,4-dihalogeno-6-pyridylethanolphenylisopropylamines for shifting the protein-fat ratio of animals in favor of protein, of the formula

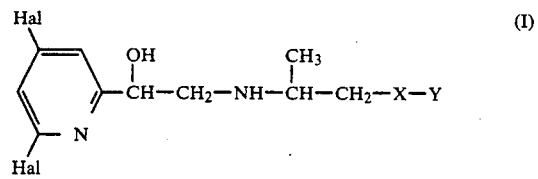

in which
Hal are identical or different and represent fluorine, chlorine or bromine,
X represents a direct bond or —$CH_2$— and
Y represents phenyl, which is substituted by OH, $C_{1-4}$-alkoxy, $C_{1-4}$-alkoxy-$C_{1-4}$-alkoxy, carboxyl, aminocarbonyl, $C_{1-4}$-alkoxycarbonyl, hydroxy-$C_{1-4}$-alkoxy, $C_{1-4}$-alkoxycarbonyl-$C_{1-4}$-alkoxy or phenyl-$C_{1-4}$-alkoxy, or their physiologically tolerated salts.

8 Claims, No Drawings

2,4-DIHALOGENO-6-PYRIDYLETHANOL-PHENYLISOPROPYLAMINES FOR SHIFTING THE PROTEIN-FAT RATIO OF ANIMALS IN FAVOR OF PROTEIN

The present invention relates to new 2,4-dihalogeno-6-pyridylethanolphenylisopropylamines, processes for their preparation and their use for shifting the protein-fat ration in favor of protein and for treating adiposity in humans and animals.

2-Halogeno-6-pyridylethanolphenylisopropylamines are already known. They are suitable as growth promoters in animals (EP-OS (European Published Specification) 170,538, 254,856 and 256,420).

Thus, for example, the following compounds are known from EP-OS (European Published Specification) 254,856;

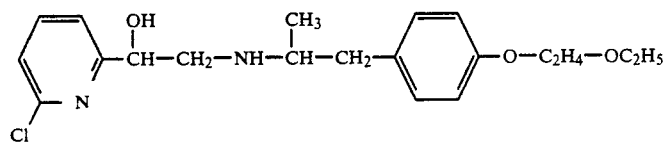

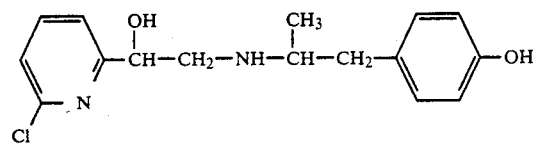

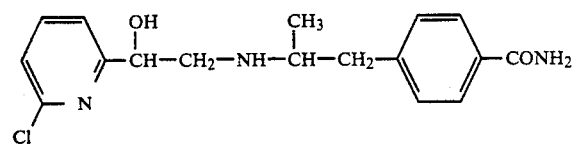

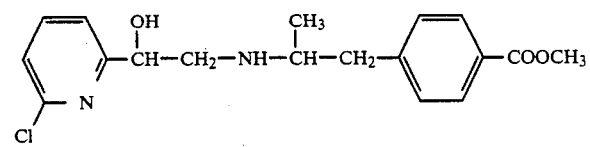

These compounds have a lipolytic action but exhibit a marked increasing influence on heart rate in dogs. Their use as agents for influencing fat metabolism is impeded by this action on the circulation. The present invention relates to 1. 2,4-Dihalogeno-6-pyridyl-ethanolamines of the formula I

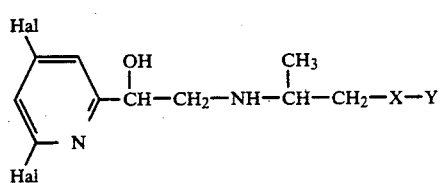

in which
Hal are identical or different and represent fluorine, chlorine or bromine,
X represents a direct bond or -CH$_2$- and
Y represents phenyl, which is substituted by OH, C$_{1-4}$-alkoxy, C$_{1-4}$alkoxy-C$_{1-4}$-alkoxy, carboxyl, aminocarbonyl, C$_{1-4}$-alkoxycarbonyl, hydroxy-C$_{1-4}$-alkoxy, C$_{1-4}$-alkoxycarbonyl-C$_{1-4-alkoxy\ or\ phenyl-C_1}$-C$_4$-alkoxy, and their physiologically tolerated salts and N-oxides.

2. Processes for the preparation of the compounds of the formula I

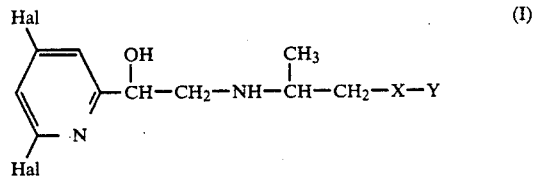

in which
Hal are identical or different and represent fluorine, chlorine or bromine,
X represents a direct bond or -CH$_2$- and
Y represents phenyl, which is substituted by OH, C$_{1-4}$-alkoxy, C$_{1-4}$-alkoxy-C$_{1-4}$-alkoxy, carboxyl, aminocarbonyl, C$_{1-4}$-alkoxycarbonyl, hydroxy-C$_{1-4}$-alkoxy, C$_{1-4}$-alkoxycarbonyl-C$_{1-4}$-alkoxy or phenyl-C$_{1-4}$-alkoxy, (a) in which halogenomethyl ketones of the formula II

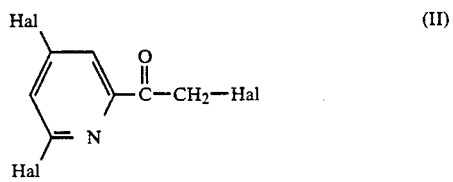

in which
Hal represents halogen,
are reacted with amines of the formula III

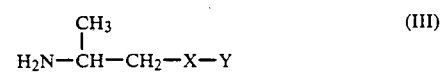

in which
X and Y have the abovementioned meanings,
and the carbonyl group is then reduced, or
(b) in which epoxides of the formula IV

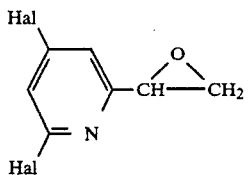 (IV)

in which
Hal represents halogen and
$R^1$, $R^2$ and $R^3$ have the abovementioned meanings,
are reacted with amines of the formula III

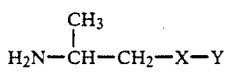 (III)

in which
X and Y have the abovementioned meanings, or
(c) in which β-halogenoethyl compounds of the formula V

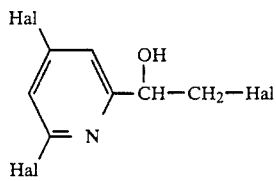 (V)

in which
Hal represents halogen,
are reacted with amines of the formula III

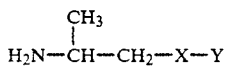 (III)

in which
X and Y have the abovementioned meanings, or
(d) compounds of the formula VI

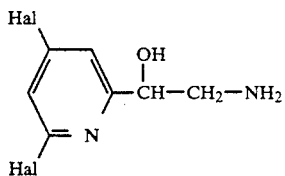 (VI)

in which
Hal represents halogen,
are reacted with ketones of the formula VII

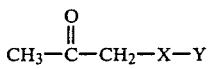 (VII)

in which
X and Y have the abovementioned meanings,
under reducing conditions, or
(e) in which compounds of the formula VIII

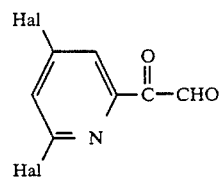 (VIII)

in which
Hal represents halogen,
are reacted with amines of the formula III

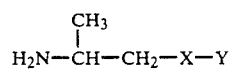 (III)

in which
X and Y have the abovementioned meanings,
under reducing conditions, or
(f) in which compounds of the formula IX

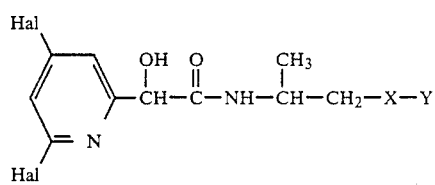 (IX)

in which
Hal, X and Y have the abovementioned meanings,
are reduced.
New compounds of the formula IX

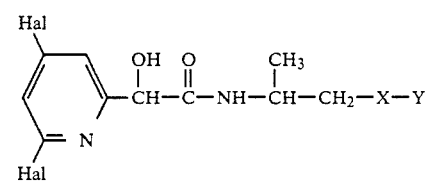 (IX)

in which
Hal, X and Y have the meanings given in the case of the compounds of the formula I.

4. Process for the preparation of compounds of the formula IX, characterized in that compounds of the formula X

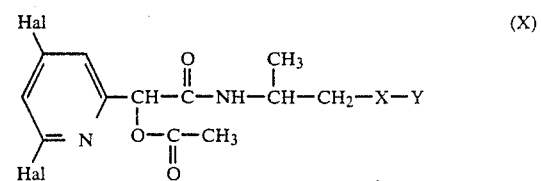 (X)

in which
Hal, X and Y have the abovementioned meanings,
are hydrolyzed.

5. New compounds of the formula X

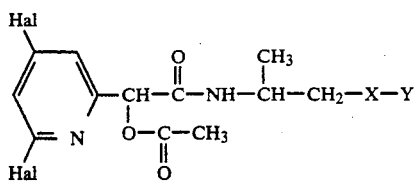

in which

Hal, X and Y have the abovementioned meanings.

6. Process for the preparation of the compounds of the formula X, characterized in that aldehydes of the formula XI

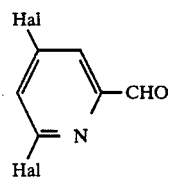

in which

Hal represents halogen and
$R^1$, $R^2$ and $R^3$ have the abovementioned meanings, are reacted with isonitriles of the formula XII

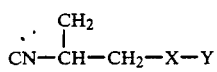

in which

X and Y have the abovementioned meanings, in the presence of acetic acid.

7. New compounds of the formula II

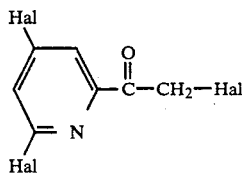

in which

Hal represents halogen.

8. Process for the preparation of the compounds of the formula II, characterized in that acetyl compounds of the formula XIII

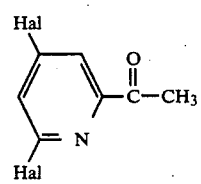

in which

Hal represents halogen, (a) are reacted with elemental halogen, if appropriate in the presence of a catalyst, or are reacted (b) with copper halides of the formula $$Cu\ Hal_2$$

(c) or with inorganic halides of the formula $SO_2Hal_2$.

New pyridylacetyl compounds of the formula XIII

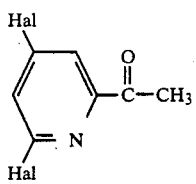

in which

Hal represents halogen.

10. Process for the preparation of the pyridylacetyl compounds of the formula XIII

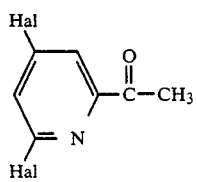

in which

Hal represents halogen,
characterized in that 2,4-dihalogeno-6-pyridylcarboxylic acid is reacted with methyllithium.

11. New compounds of the formula IV

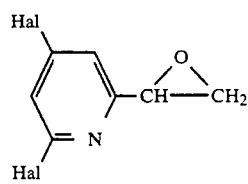

in which

Hal represents naiogen.

12. Process for the preparation of the compounds of the formula IV

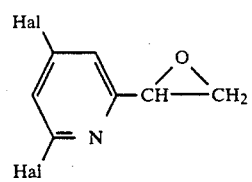

in which

Hal represents halogen, characterized in that
(a) compounds of the formula V

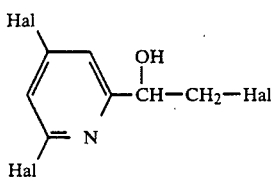

in which

Hal represents halogen, are reacted with bases, or
(b) aldehydes of the formula XI

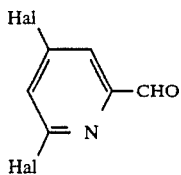

(XI)

in which
Hal represents halogen,
are reacted with reagents which transfer methyl groups, in the presence of bases under the conditions of Corey epoxidation.

13. New compounds of the formula V

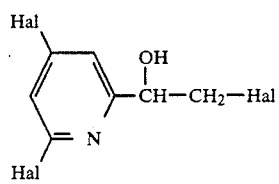

(V)

in which
Hal represents halogen.

14. Process for the preparation of the compounds of the formula V

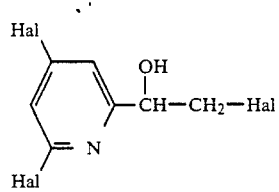

(V)

in which
Hal represents halogen, characterized in that compounds of the formula II
in which
Hal represents halogen,
are reduced.

15. New compounds of the formula VI

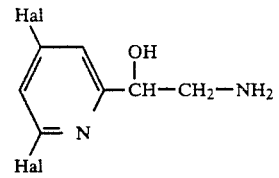

(VI)

in which
Hal represents halogen.

16. Process for the preparation of the compounds of the formula VI

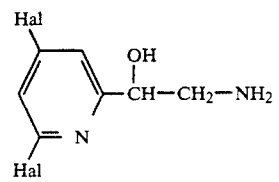

(VI)

in which

Hal represents halogen, characterized in that cyanohydrins of the formula XIV

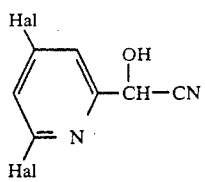

(XIV)

in which
Hal represents halogen,
are reduced.

17. New compounds of the formula XIV

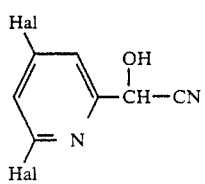

(XIV)

in which
Hal represents halogen.

18. Process for the preparation of the new compounds of the formula XIV

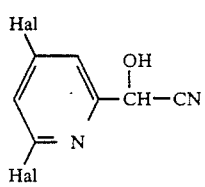

(XIV)

in which
Hal represents halogen,
characterized in that compounds of the formula XI

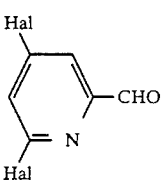

(XI)

in which
Hal represents halogen,
are reacted with HCN, or cyanide salts.

19. New compounds of the formula VIII

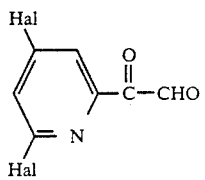

(VIII)

in which
Hal represents halogen.

20. Process for the preparation of the new compounds of the formula VIII

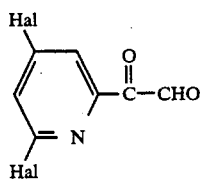

(VIII)

in which
  Hal represents halogen,
characterized in that compounds of the formula V

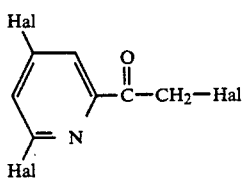

(V)

in which
  Hal represents halogen,
are oxidized.

The compounds of the formula I can be present in the form of their steric and optical isomers and in this way result in forms which are enantiomeric and/or diastereomeric to one another.

Physiologically tolerated salts of the compounds of the formula I can be formed with the following acids: hydrochloric acid, sulphuric acid, phosphoric acid, perchloric acid, bromic and hydriodic acid, nitric acid, acetic acid, oxalic acid, malonic acid, succinic acid, ascorbic acid, malic acid, tartaric acid, maleic acid, fumaric acid, methanesulphonic acid, benzoic acid, substituted benzoic acids, formic acid, toluenesulphonic acid, benzenesulphonic acid, phthalic acid, naphthalenesulphonic acid, nicotinic acid, palmitic acid and embonic acid.

Preferred compounds of the formula I are those in which
  Hal represents fluorine, chlorine or bromine, in particular chlorine,
  X represents a direct bond and
  Y represents phenyl, which is substituted by hydroxyl, methoxy, ethoxy, hydroxyethoxy, methoxyethoxy, ethoxyethoxy, methoxycarbonylmethoxy, ethoxycarbonylethoxy, phenylethyleneoxy or phenylpropyleneoxy.

Particularly preferred compounds of the formula I are those in which
  Hal represents chlorine,
  Y represents phenyl, which is substituted in the 4-position by hydroxyl, methoxy, ethoxy, hydroxyethoxy, methoxyethoxy, ethoxyethoxy, methoxycarbonylmethoxy or ethoxycarbonylethoxy.

Compounds which may be mentioned specifically

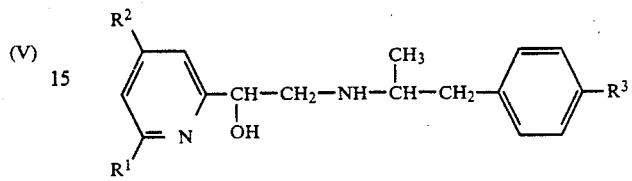

| $R^1$ | $R^2$ | $R^3$ |
|---|---|---|
| Cl | Cl | $OCH_2CH_2OH$ |
| Cl | Cl | $OCH_2COOCH_3$ |
| Cl | Cl | $OCH_2COOH$ |
| Cl | Cl | $COOC_2H_5$ |
| Cl | Br | $OCH_2CH_2NH_2$ |
| Br | Br | $COOCH_3$ |
| Cl | Br | $OCH_2COOCH_3$ |
| Br | Br | $OCH_2COOCH_3$ |
| Cl | Cl | $COOCH_3$ |
| Br | Br | $OCH_2COOH$ |

The salts with hydrochloric acid, sulphuric acid, phosphoric acid, oxalic acid, maleic acid, fumaric acid and malonic acid may be mentioned as preferred.

The compounds of the formula I can be prepared by the processes (a) to (f) described above under 2.

If 2-chloroacetyl-4,6-dichloropyridine is employed as the halogenomethyl ketone of the formula II and 1-(4-methoxycarbonylphenyl)isopropylamine is employed as the amine of the formula III in process (2a), process (a) can be represented by the following equation:

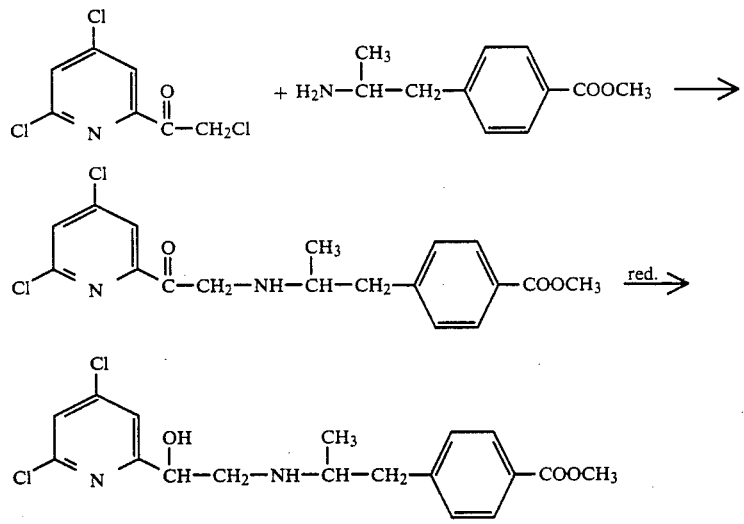

The compounds of the formula II are prepared by the process described under (8), by reacting the corresponding acetyl-substituted heteroaryl compounds with elemental halogen, an inorganic acid halide or with copper halides in a manner which is known per se.

The substituents Hal in formula II preferably have the preferred meanings given above in the case of the compounds of the formula I. The following compounds of the formula II may be mentioned specifically: 2,4-dichloro-6-pyridyl chloromethyl ketone, 2,4-dichloro-6-pyridyl bromomethyl ketone, 2,4-dibromo-6-pyridyl-bromomethyl ketone and 2,4-difluoro-6-pyridyl chloromethyl ketone.

The amines of the formula III are known (compare, for example, EP-OS (European Published Specification) 70,133), or they can be prepared by processes analogous to known processes. The substituents X and Y preferably have the preferred meanings given above in the case of the compounds of the formula I. The following compounds of the formula III may be mentioned specifically:

H₂N—CH(CH₃)—X—⟨C₆H₄⟩—R³

| X | R³ |
|---|---|
| —CH₂— | OCH₂CH₂—O—C₂H₄ |
| —CH₂— | OCH₂COOCH₃ |
| —CH₂— | OCH₂COOH |
| —CH₂— | OCH₂CH₂OH |
| —(CH₂)₂— | OCH₂COOC₂H₅ |

The following reducing agents may be mentioned as reducing agents for carrying out process (2a): H₂/catalyst, examples which may be mentioned of the catalyst are: PtO₂ and Pd-on-active charcoal; and complex metal hydrides, such as, for example, LiAlH₄, NaBH₄ and NaBH₃CN.

The following reducing agents are particularly preferably employed: NaBH₄ and NaBH₃CN Process (2a) is carried out by bringing together compounds II and III in a diluent in an approximately equimolar ratio.

The reaction is preferably carried out at temperatures from −20° C. to +100° C.

The reaction is preferably carried out under normal pressure.

All the inert organic solvents are used as the diluent. These include, in particular, aliphatic and aromatic hydrocarbons, such as pentane, hexane, cyclohexane, petroleum ether, ligroin, benzene and toluene; chlorinated hydrocarbons, such as methylene chloride, ethylene chloride and chloroform; ethers, such as diethyl ether and glycol dimethyl ether; nitriles, such as acetonitrile, propionitrile and benzonitrile; and alcohols, such as methanol, ethanol and n- and i-propanol.

Alcohols are preferred, it being possible for the reduction to be carried out immediately without isolation of the intermediate stages.

If 2,4-dichloropyridine 6-epoxide is employed as the epoxide of the formula IV and 3-(4-ethoxycarbonylmethoxyphenyl)-2-aminopropane is employed as the amine of the formula III in process (2b), process (2b) can be represented by the following equation:

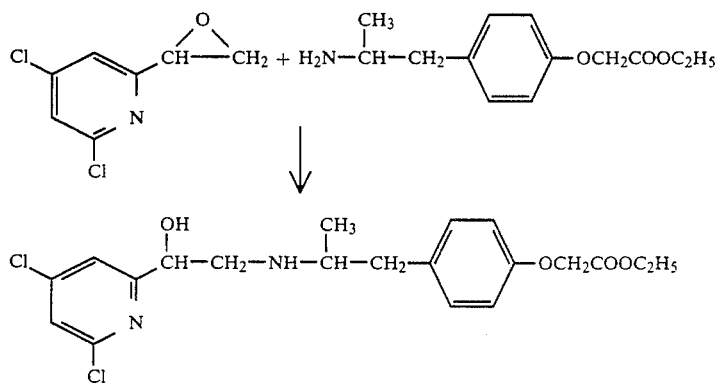

Epoxides of the formula IV are prepared by the process described under (12).

The following epoxides may be mentioned specifically:
2,4-dichloro-pyridine 6-epoxide and
2,4-dibromo-pyridine 6-epoxide.

Process (2) is carried out by reacting approximately equimolar amounts of the epoxide of the formula IV and the amine of the formula III in a diluent.

In general, an excess of amine (1–3 molar, preferably 1–1.5 molar) with respect to the epoxide of the formula IV is used.

The reaction is carried out at temperatures from +20° to +150° C.

The reaction is preferably carried out under normal pressure.

All the inert organic solvents are used as the diluent. These include, in particular, aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, and furthermore ethers, such as diethyl ether, dibutyl ether, glycol dimethyl ether, diglycol dimethyl ether, tetrahydrofuran and dioxane, and furthermore nitriles, such as acetonitrile and benzonitrile, amides, such as dimethylformamide, and alcohols, such as methanol, ethanol and n-and i-propanol.

Alcohols are preferred.

If 2,4-dibromo-6-(1-hydroxy-2-chloroethyl)-pyridine is employed as the β-halogenomethyl compound of the formula V and 2-(4-methoxyphenyl)-1-methylethylamine is employed as the amine of the formula III in process (2c), process (c) can be represented by the following equation:

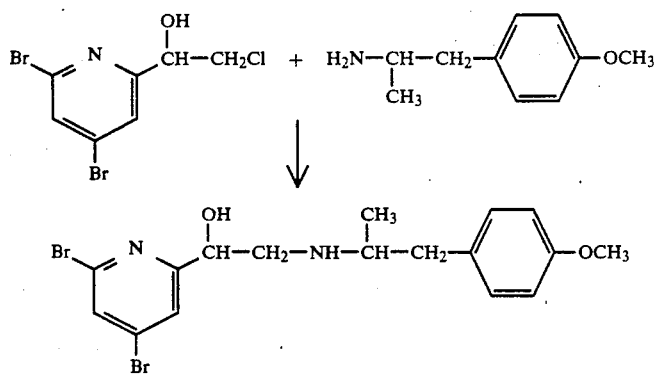

The preparation of the β-halogenomethyl compounds of the formula V is carried out by the process described under 14.

The following compounds of the formula V may be mentioned specifically:

1-(2,4-dibromo-6-pyridyl)-2-chloroethanol,
1-(2,4-difluoro-6-pyridyl)-2-chloroethanol,
1-(2,4-dichloro-6-pyridyl)-2-chloroethanol, and
1-(2,4-dichloro-6-pyridyl)-2-bromoethanol.

Process 2c) is carried out by reacting the betahalogenomethyl compound of the formula V with excess amine of the formula III, if appropriate in the presence of a diluent.

The reaction is carried out at temperatures from +20° to +150° C.

The reaction is carried out under normal pressure or under increased pressure.

All the inert organic solvents are used as the diluent. These include, in particular, aliphatic and aromatic, optionally halogenated hydrocarbons, such as pentane, hexane, cyclohexane, benzene, toluene, methylene chloride and chloroform, and furthermore ethers, such as diethyl ether, tetrahydrofuran and dioxane, and moreover nitriles, such as acetonitrile and benzonitrile, and furthermore amides, such as dimethylformamide, and furthermore alcohols, such as methanol, ethanol and n-and i-propanol.

Alcohols are preferably employed.

If 2,4-difluoro-6-(1-hydroxy-2-aminoethyl)pyridine is employed as the compound of the formula VI and (3-chloro-4-methoxyphenyl)-acetone is employed as the compound of the formula VII in process (2d), process (d) can be represented by the following equation:

The compounds of the formula VI are prepared by the process described under (16).

The following compounds of the formula VI may be mentioned specifically:

1-(2,4-dibromo-6-pyridyl)-2-aminoethanol,
1-(2,4-difluoro-6-pyridyl)-2-aminoethanol and
1-(2,4-dichloro-3-amino-6-pyridyl)-2-aminoethanol.

The compounds of the formula VII are known (compare, for example, EP-OS (European Published Specification) 23,385, DE-OS (German Published Specification) 2,034,277 and PCT Application WO 84 00 956), or they can be prepared analogously to known compounds.

The following compounds of the formula VII may be mentioned specifically:

$$CH_3-\overset{O}{\underset{\|}{C}}-X-\underset{\diagdown}{\diagup}-R^3$$

| X | $R^3$ |
|---|---|
| $-CH_2-$ | $-OCH_2CH_2-O-C_2H_4$ |
| $-CH_2-$ | $-COOCH_3$ |
| $-CH_2-$ | $-OCH_2COOCH_3$ |
| $-CH_2-$ | $-OCH_2CH_2OH$ |
| $-(CH_2)_2-$ | $-COOH$ |
| $-CH_2-$ | $-OCH_2COOH$ |

Process (2d) is carried out by initially introducing approximately equimolar amounts of the compounds of the formulae VI and VII into a diluent and reducing the mixture.

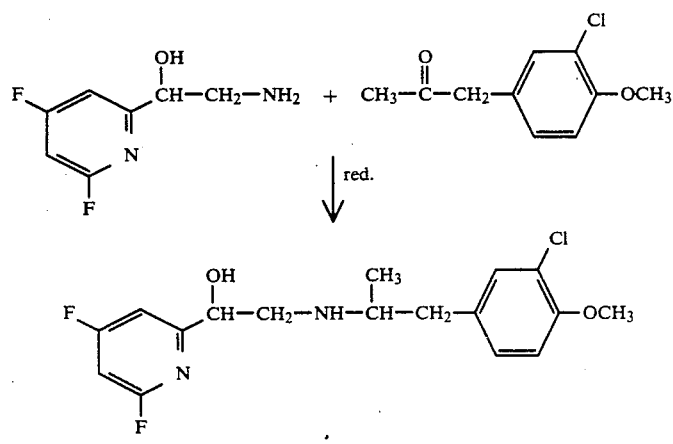

The reaction is carried out at temperatures from 0° C. to 150° C.

The reaction is preferably carried out under normal pressure.

All the inert organic solvents are used as the diluent. These include aliphatic and aromatic optionally halogenated hydrocarbons, such as pentane, hexane, cyclohexane, benzene, toluene, methylene chloride, ethylene chloride, chloroform and chlorobenzene, and furthermore ethers, such as diethyl ether, tetrahydrofuran and dioxane, and moreover nitriles, such as acetonitrile and benzonitrile, amides, such as dimethylformamide, and alcohols, such as methanol and ethanol. Alcohols are preferably employed.

The reducing agents used are: $H_2$/catalyst, and an example which may be mentioned of the catalyst is $PtO_2$; and complex metal hydrides, such as, for example, $LiAlH_4$, $NaBH_4$ and $NaBH_3CN$. Catalysts which are particularly preferably employed are: $NaBH_4$ and $NaBH_3CN$.

If 2,4-dibromo-6-pyridylglyoxal is employed as the compound of the formula VIII and 1-(4-methoxyphenyl)isopropylamine is employed as the amine of the formula III in process (2e), process (e) can be represented by the following equation:

2,4-dichloro-6-pyridylglyoxal.

Process (2e) is carried out by adding about the equivalent amount of the amine of the formula III to the compound of the formula VIII in a diluent and then reducing the mixture.

The reaction is carried out at temperatures from 0° C. to 100° C.

The reaction is preferably carried out under normal pressure.

All the inert organic solvents are used as the diluent. These include, in particular, aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, and furthermore ethers, such as diethyl ether, dibutyl ether, glycol dimethyl ether, diglycol dimethyl ether, tetrahydrofuran and dioxane, and in addition esters, such as methyl and ethyl acetate, and furthermore nitriles, such as, for example, acetonitrile, propionitrile, benzonitrile and glutaric acid dinitrile, and moreover amides, such as, for example, dimethylformamide, dimethylacetamide and N-methylpyrrolidone, as well as tetramethylene sulphone and hexamethylphosphoric acid triamide, and

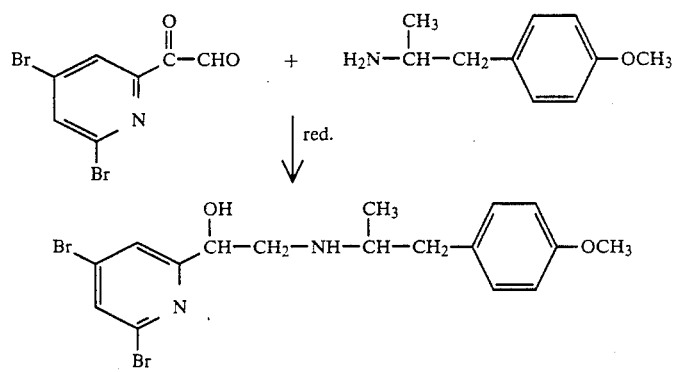

The preparation of the compounds of the formula VIII is carried out by the process described under (20). Compounds of the formula III are known (compare, for example, EP-OS (European Published Specification) 70,133), or can be prepared analogously to known compounds The following compounds of the formula VIII may be mentioned specifically:
2,4-dibromo-6-pyridylglyoxal,
2,4-difluoro-6-pyridylglyoxal and moreover alcohols, such as methanol, ethanol and n- and i-propanol.

The reducing agents used are: $H_2$/catalyst; $PtO_2$ and Pd-on-charcoal may be mentioned as the catalyst, and furthermore complex metal hydrides, such as $LiAlH_4$ and $NaBH_4$.

If (2,4-dichloro-6-pyridyl)hydroxyacetic acid 1-(4-methoxyphenyl)isopropyl-amide is employed as the compound of the formula X in process 2f), the process can be represented by the following equation:

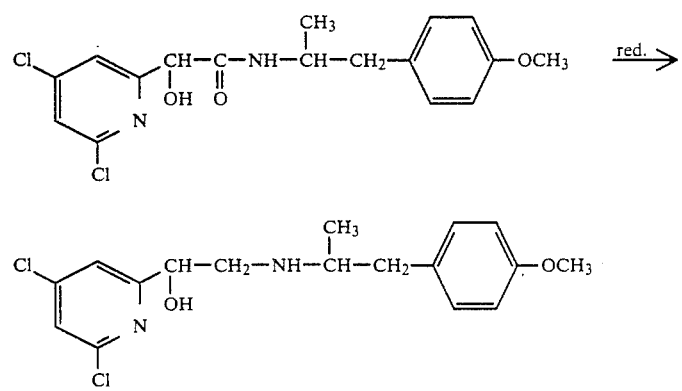

The compounds of the formula X are new. Their preparation is described under (4). The following compounds of the formula X may be mentioned specifically:

(2,4-dichloro-6-pyridyl)hydroxyaceticacid(3-(4-methoxycarbonylmethoxyphenyl)-2-propyl)amide (2,4-dichloro-6-pyridyl)hydroxyacetic acid (3-(4-ethoxycarbonylphenyl)-2-propyl)amide (2,4-dibromo-6-pyridyl)hydroxyacetic acid (3-(4-methoxycarbonylmethoxyphenyl)-2-propyl)amide (2,4-dichloro-6-pyridyl)hydroxyacetic acid (3-(4-ethoxycarbonylmethoxyphenyl)-2-propyl)amide (2, ibromo-6-pyridyl)hydroxyacetic acid (3-(4-methoxycarbonylphenyl)-2-propyl)amide (3,4dibromo-6-pyridyl)hydroxyacetic acid (3-(4-ethoxycarbonylmethoxyphenyl)-2-propyl)amide.

Process (2f) is carried out by reacting the compound of the formula X with excess reducing agent in a diluent.

The reaction is carried out at temperatures from 0° C. to +150° C.

The reaction is preferably carried out under normal pressure.

All the inert organic solvents are used as the diluent. These include, in particular, aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, and furthermore ethers, such as diethyl ether, dibutyl, ether, glycol dimethyl ether, diglycol dimethyl ether, tetrahydrofuran and dioxane.

Complex metal hydrides, such as LiAlH$_4$, and boranes, such as diborane, are used as the reducing agent.

Compounds of the formula IX are obtainable by process 4.

If (2,4-dichloro-6-pyridyl)-acetoxyacetic acid (2-(-4-ethoxyphenyl)ethylamide is employed as the compound of the formula X in process (4), the process can be represented by the following equation:

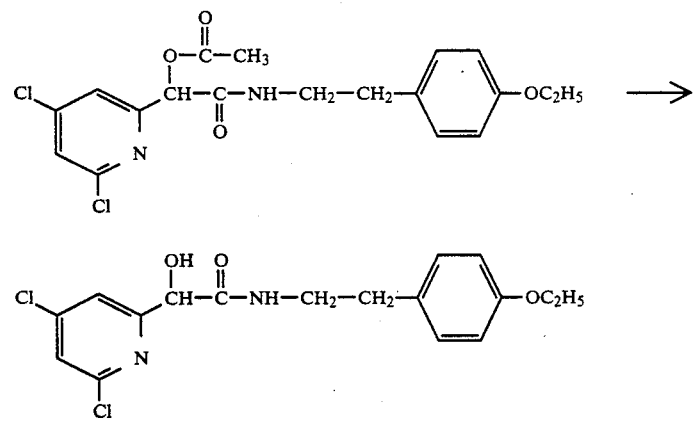

The compounds of the formula X are new. Their preparation is carried out by the process described under (6). The following compounds of the formula X may be mentioned specifically:

(2,4-dichloro-6-pyridyl)acetoxyacetic acid (3-(4-methoxycarbonylmethoxyphenyl)-2-propyl)amide (2,4-dichloro-6-pyridyl)acetoxyacetic acid (3-(4-ethoxycarbonylphenyl)-2-propyl)amide (2,4-dibromo-6-pyridyl)acetoxyacetic acid (3-(4-methoxycarbonylmethoxyphenyl)-2-propyl)amide (2,4-dichloro-6-pyridyl)acetoxyacetic acid (3-(4-ethoxycarbonylmethoxyphenyl)-2-propyl)amide (2,4-dibromo-6-pyridyl)acetoxyacetic acid (3-(4-methoxycarbonylphenyl)-2-propyl)amide (2,4-dibromo-6-pyridyl)acetoxyacetic acid (3-(4-ethoxycarbonylmethoxyphenyl)-2-propyl)amide (2,4-difluoro-6-pyridyl)acetoxyacetic acid(3-(4-methoxycarbonylphenyl)-2-propyl)amide.

Inorganic acids or alkalis are used to split off the acetyl group. These include hydrogen halide acids, such as hydrochloric acid; and sulphuric acid, phosphoric acid, NaOH and KOH.

The process is carried out by treating the compound X in a diluent, as a solubilizing agent, with an excess of aqueous solution of the inorganic acid or alkali.

The reaction is carried out at temperatures from 20° C. to +150° C.

The reaction is preferably carried out under normal pressure.

All the inert organic solvents which are water-miscible can be used as the diluent. These include ethers, such as tetrahydrofuran and dioxane; nitriles, such as acetonitrile; amides, such as dimethylformamide; alcohols, such as methanol and ethanol; and dimethyl sulphoxide.

Compounds of the formula X are obtainable by process (6).

If 2,4-difluoro-pyridine-6-aldehyde is employed as the compound of the formula XI and 3-(4-methoxyphenyl)-2-propylisonitrile is employed as the isonitrile of the formula XIII in process (6), the process can be represented by the following equation:

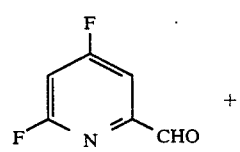 +

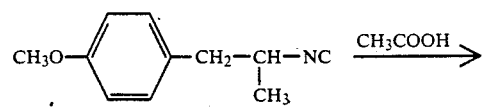

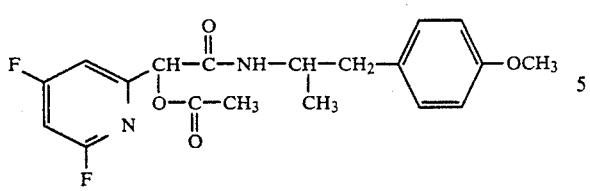

Aldehydes of the formula XI are known, for example from J. Graf, J. Pr. Chem. (2) 134 (1932), pages 177, 180, or they can be prepared by processes analogous to known processes. The following compounds of the formula XI may be mentioned specifically:
2,4-dichloropyridine-6-aldehyde
2,4-dibromopyridine-6-aldehyde
2,4-difluoropyridine-6-aldehyde Isonitriles of the formula XII are known (I. Ugi et al., Angew. Chem. 77 (1965), 492), or they can be prepared by processes analogous to known processes. The following compounds of the formula XII may be mentioned specifically:

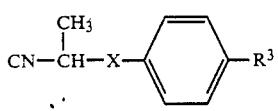

| X | R³ |
|---|---|
| —CH₂— | —O—CH₂CH₂—O—C₂H₅ |
| —CH₂— | —COOCH₃ |
| —CH₂— | —OCH₂COOCH₃ |
| —CH₂— | —OCH₃ |
| —(CH₂)₂— | —OCH₂CH₂OH |

The process is carried out by reacting the compound XI with twice the molar amount of the isonitrile of the formula XII and acetic acid in a diluent.

The reaction is carried out at temperatures from 0° C. to +150° C.

The reaction is preferably carried out under normal pressure.

All the inert organic solvents are used as the diluent. These include, in particular, optionally halogenated aliphatic and aromatic hydrocarbons, such as pentane, hexane, cyclohexane, benzene, toluene, methylene chloride, chloroform and chlorobenzene; ethers, such as diethyl ether and tetrahydrofuran; and nitriles, such as acetonitrile and benzonitrile.

Compounds of the formula II are obtainable by processes 8 a and b.

If 2,4-dichloro-6-acetylpyridine is employed as the compound of the formula XIII and bromine is employed the halogen Hal in process (8a), the reaction can be represented by the following equation:

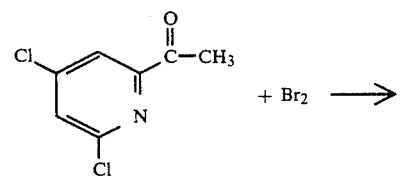 + Br₂ ⟶

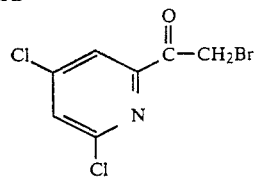

The compounds of the formula XIII are new. Their preparation is carried out by the process described under (10).

The following compounds of the formula XIII may be mentioned specifically:
2,4-dichloro-6-acetylpyridine,
2,4-dibromo-6-acetylpyridine.

Process (8a) is carried out by adding the equivalent amount of halogen, if appropriate dissolved in a diluent, to the compound XIII in a diluent.

The reaction is carried out at +20° C. to +150° C., preferably at the boiling point of the diluent used.

The reaction is preferably carried out under normal pressure.

Diluents which may be mentioned are: aliphatic, optionally halogenated hydrocarbons, such as pentane, hexane, heptane, cyclohexane, methylene chloride, ethylene chloride, chloroform and carbon tetrachloride, alcohols, such as methanol and ethanol, esters, such as ethyl acetate, and mixtures of these diluents.

If 2,4-dibromo-6-acetylpyridine is employed as the compound of the formula XIII and copper(II) bromide employed as the compound of the formula CuHal₂ in process (8b), the reaction can be represented by the following equation:

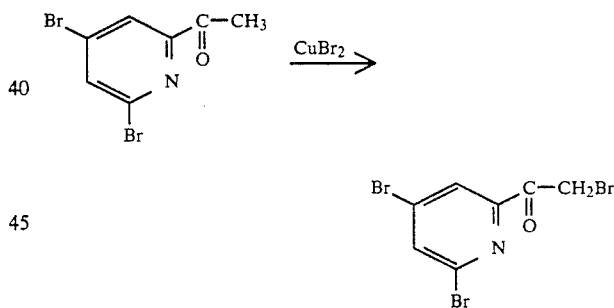

Process (8b) is carried out by heating equivalent amounts of the compound of the formula XI and the compound CuHal₂ under reflux in the diluent for 1–24 hours, preferably 6–12 hours.

The reaction is otherwise carried out as described in the case of process (8a).

If 2,4-dichloro-6-acetyl-pyridine is employed as the compound of the formula (XIII) and SO₂Cl₂ is employed as the inorganic acid halide in process (8c), the reaction can be represented by the following equation:

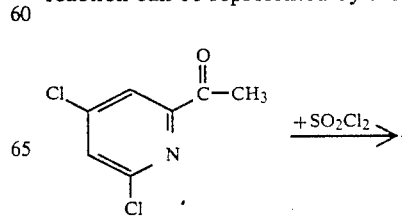 +SO₂Cl₂ ⟶

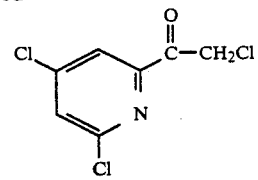

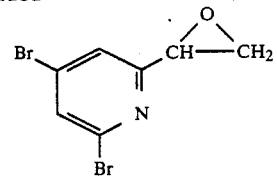

The reaction is otherwise carried out as described in the case of process (8a).

Pyridylacetyl compounds of the formula XIII are obtainable by the process described under (10). Process (10) can be carried out as described in U.S Pat. No. 4,358,455. The 2,4-dihalogeno-6-pyridyl-carboxylic acids employed as the starting substance are known or can be prepared by processes analogous to known processes (Graf, J. Pr. Chem. (2) 134 (1932) pages 177–187).

Epoxides of the formula IV are obtainable by the processes described in (12).

Process (12a) is carried out by reacting the compound of the formula V with 2–5 times the molar amount, preferably 2–4 times the molar amount, of a base in a diluent. If 1-(2,4-dichloro-6-pyridyl)-2-bromoethanol is employed as the compound of the formula V and NaOH is employed as the base, the reaction can be represented by the following equation:

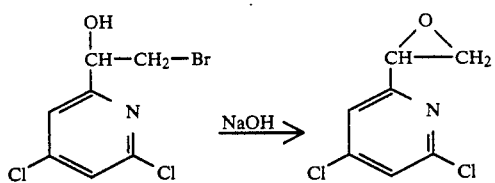

The following compounds of the formula V may be mentioned specifically:
1-(2,4-dichloro-6-pyridyl)-2-bromoethanol,
1-(2,4-dichloro-6-pyridyl)-2-chloroethanol.

Bases which may be mentioned are: alkali metal and alkaline earth metal hydroxides, such as sodium hydroxide and potassium hydroxide; carbonates and bicarbonates, such as sodium carbonate, sodium bicarbonate and barium carbonate; and alcoholates, such (as sodium methylate and sodium ethylate.

Diluents which may be mentioned are alcohols, such as methanol and ethanol, water and mixtures of alcohols with water.

The reaction is carried out at temperatures from 0° C. to +100° C., and is preferably carried out under normal pressure.

If 2,4-dibromopyridine-6-aldehyde is employed as the aldehyde of the formula XI, trimethylsulphonium iodide is employed as the reagent which transfers methylene groups and sodium hydride is employed as the base in process (12b), the reaction can be represented by the following equation:

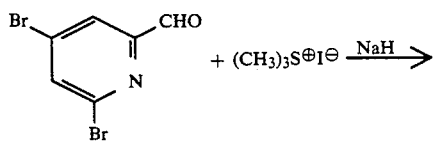 + $(CH_3)_3S^{\oplus}I^{\ominus}$ $\xrightarrow{NaH}$

The following compounds of the formula XII may be mentioned specifically:
2,4-dichloropyridine-6-aldehyde,
2,4-dibromopyridine-6-aldehyde,
2,4-difluoropyridine-6-aldehyde.

Reagents which may be mentioned which transfer methylene groups are: trimethylsulphonium halides, such as trimethylsulphonium chloride, bromide and iodide, and trimethylsulphoxonium halides, such as trimethylsulphoxonium chloride, bromide and iodide.

The bases used are: alkali metal and alkaline earth metal hydrides, such as sodium hydride, and alkali metal and alkaline earth metal alcoholates, such as potassium tert.-butylate.

Process (12b) is carried out by initially introducing 1.1 equivalents of the base into dimethyl sulphoxide, then adding the agent which transfers methylene groups (1.1 equivalents) and finally adding 1 equivalent of the compound of the formula XII.

The reaction is carried out at temperatures from 0° C. to 100° C., preferably from 50°–70° C., and is preferably carried out under normal pressure.

The diluents employed are dimethyl sulphoxide or mixtures of dimethyl sulphoxide with inert organic solvents.

Inert organic solvents which may be mentioned are: ethers, such as diethyl ether, tetrahydrofuran and dioxane.

Compounds of the formula V are obtainable by process (14).

If 2,4-dichloro-6-pyridyl chloromethyl ketone is employed as the compound of the formula II in process (14), process (14) can be represented by the following equation:

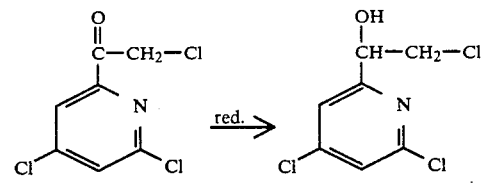

The compounds of the formula II are new and are obtained by the processes mentioned under (8). Compounds of the formula II which are mentioned in process (2a) are preferably employed.

Reducing agents for carrying out process (14) which may be mentioned are: $H_2$/catalyst, and catalysts which may be mentioned are: $PtO_2$ and Pd-on-charcoal; and complex metal hydrides, such as, for example, $LiAlH_4$, $NaBH_4$ and $NaBH_3CN$. $NaBH_4$ and $NaBH_3CN$ are preferably employed.

Process (14) is carried out by reacting the compound II with the reducing agent in a diluent.

The reaction is carried out at temperatures from −20° C. to +100° C.

The reaction is preferably carried out under normal pressure.

All the inert organic solvents are used as the diluent. These include, in particular, optionally halogenated aliphatic and aromatic hydrocarbons, such as pentane, hexane, cyclohexane, benzene, toluene, methylene chloride, chloroform and chlorobenzene; ethers, such as diethyl ether and tetrahydrofuran; nitriles, such as acetonitrile and benzonitrile; and alcohols, such as methanol, ethanol and n- and i-propanol..Alcohols are preferably employed.

Compounds of the formula VI are obtainable by process (16).

If 2,4-dichloro-6-pyridylcyanohydrin is employed as the compound of the formula XIV in process (16), the process can be represented by the following equation:

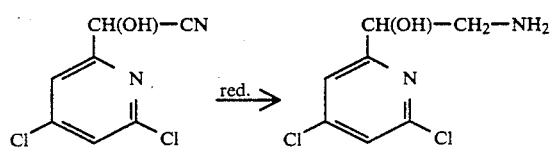

The compounds of the formula XIV are new. Their preparation is described below. The following compounds of the formula XIV may be mentioned specifically:
(2,4-dichloro-6-pyridyl)-cyanohydrin and
(2,4-dibromo-6-pyridyl)-cyanohydrin.

The process is carried out by reducing the compound XIV in a diluent.

The reaction is carried out at temperatures from 0° C. to 150° C.

The reaction is preferably carried out under normal pressure or under increased pressure.

The diluents used are, regardless of the reducing agent, water or organic solvents or mixtures thereof. The organic solvents include aliphatic and aromatic, optionally halogenated hydrocarbons, such as pentane, hexane, cyclohexane, benzene, toluene, methylene chloride, ethylene chloride, chloroform and chlorobenzene, and furthermore ethers, such as diethyl ether, tetrahydrofuran and dioxane, and moreover nitriles, such as acetonitrile and benzonitrile, amides, such as dimethylformamide, and alcohols, such as methanol and ethanol.

The reducing agents used are: $H_2$/catalyst, and an example of a catalyst which may be mentioned is $PtO_2$; alkali metal and alkaline earth metal amalgams, such as, for example, sodium amalgam; base metals in the presence of hydrochloric acid, such as, for example, zinc/hydrochloric acid; complex metal hydrides, such as, for example, $LiAlH_4$; and boranes, such as, for example, diborane.

Compounds of the formula XIV are obtainable by process (18).

If 2,4-difluoropyridine-6-aldehyde is employed as the compound of the formula XI for carrying out process (18), the process can be represented by the following equation:

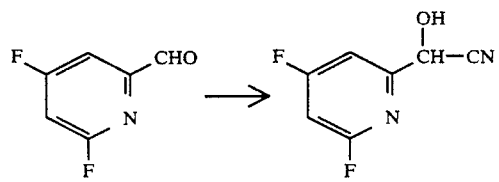

Aldehydes of the formula XI are known (R. Graf, J. Pr. Chem. 134 (1932) pages 177-187).

The following compounds of the formula XI may be mentioned specifically:
2,4-dichloropyridine-6-aldehyde and
2,4-dibromopyridine-6-aldehyde.

The process is carried out by reacting the aldehydes of the formula XI or hydrogen sulphite addition products thereof with hydrogen cyanide or its salts or lower aliphatic ketone cyanohydrins in a manner which is known from the literature (P. Kurtz, in Houben-Weyl, Volume VIII, page 274 et seq.).

Compounds of the formula VIII are obtainable by process (20).

If 2,4-dichloro-6-pyridyl bromomethyl ketone is employed as the halogenomethyl ketone in process (20), the process can be represented by the following equation:

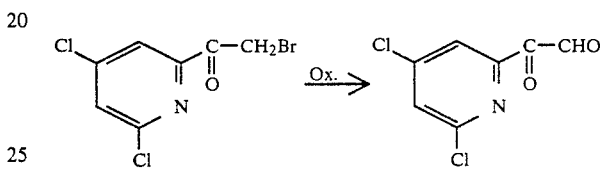

The compounds mentioned in the case of process (2) are preferably employed as the halogenomethyl ketones of the formula V.

The process is carried out by oxidizing the compounds of the formula V, if appropriate in the presence of a diluent.

The reaction is carried out at temperatures from +20° C. to +100° C.

The reaction is preferably carried out under normal pressure.

Dimethyl sulphoxide is preferably used as the oxidizing agent (N. Kornblum et al., JACS 79, 6562 (1957)).

If the reaction is carried out in the presence of a diluent, all the inert organic solvents can be used. These include, in particular, aliphatic and aromatic, optionally halogenated hydrocarbons, such as pentane, hexane, cyclohexane, benzene, toluene, methylene chloride, chloroform and chlorobenzene; ethers, such as diethyl ether and tetrahydrofuran; and nitriles, such as acetonitrile and benzonitrile. The reaction is preferably carried out in dimethyl sulphoxide without a further solvent.

The active compounds are used as growth promoters on animals for promoting and accelerating growth and milk and wool production and for improving the feed utilization and meat quality and for shifting the meat-fat ratio in favor of meat. The active compounds are used on stock, breeding and ornamental animals and pets. They are also used for the treatment of adiposity in humans and animals.

The stock and breeding animals include mammals, such as, for example, cattle, pigs, horses, sheep, goats, rabbits, hares, fallow deer and fur-bearing animals, such as mink and chinchillas, poultry, such as, for example, chickens, geese, ducks, turkeys and pigeons, fish, such as, for example, carp, trout, salmon, eels, tench and pike, and reptiles, such as, for example, snakes and crocodiles.

The ornamental animals and pets include mammals, such as dogs and cats, birds, such as parrots and canaries, and fish, such as ornamental and aquarium fish, for example goldfish.

The active compounds are employed during all the growth and performance phases of the animals, regardless of the sex of the animals.

The amount of the active compounds which is administered to the animals to achieve the desired effect can be varied widely because of the favorable properties of the active compounds. It is preferably about 0.001 to 50 mg/kg, in particular 0.01 to 5 mg/kg, of body weight per day. The appropriate amount of active compound and the appropriate duration of the administration depend in particular on the species, age, body weight, sex, degree of obesity, state of health and type of housing and feeding of the animals and can easily be determined by any expert.

The active compounds are administered to the animals by customary methods. The nature of the administration depends in particular on the species, behavior and state of nutrition and health of the animals.

Administration is effected orally or parenterally in formulations suitable for this or in the pure form. Oral formulations are powders, tablets, granules, drenches, boli and feedstuffs, premixes for feedstuffs and formulations for administration via the drinking water.

Parenteral formulations are, for example, injection solutions and implants.

The oral formulations contain the active compound in concentrations of 0.01 ppm–100%, preferably 0.01 ppm –1%.

The active compounds can be administered a single time. However, the active compounds can also be administered temporarily or continuously during the entire or during some of the growth and output phase.

In the case of continuous administration, they can be used once or several times daily at regular or irregular intervals.

The active compounds can be present in the formulations by themselves or as a mixture with other active compounds, mineral feedstuffs, trace element compounds, vitamins, nitrogen-supplying non-protein compounds, dyestuffs, antioxidants, flavorings, emulsifiers, flow control auxiliaries, preservatives and pressing auxiliaries.

Other active compounds are:

for example antibiotics, such as tylosin and virginiamycin.

Mineral feedstuffs are, for example, dicalcium phosphate, magnesium oxide and sodium chloride.

Trace element compounds are, for example, iron fumarate, sodium iodide, cobalt chloride, copper sulphate and zinc oxide.

Vitamins are, for example, vitamin A, vitamin D:, vitamin E, B vitamins and vitamin C.

Nitrogen-supplying non-protein compounds are, for example, biuret and urea.

Dyestuffs are, for example carotinoids, such as citranaxanthine, zeaxanthine and capsanthine.

Antioxidants are, for example, ethoxyquin and butylhydroxy-toluene.

Flavorings are, for example, vanillin.

Emulsifiers are, for example, esters of lactic acid and lecithin.

Flow control auxiliaries are, for example, sodium stearate and calcium stearate.

Preservatives are, for example citric acid and propionic acid.

Pressing auxiliaries are, for example, lignin-sulphonates and cellulose ethers.

The active compounds can also be administered together with the feed and/or the drinking water.

Feed includes individual feedstuffs of vegetable origin, such as hay, beet and cereal by-products, individual feedstuffs of animal origin, such as meat, fats, milk products, bonemeal and fish products, and the individual feedstuffs, such as vitamins, proteins, amino acids, for example DL-methionine, and salts, such as lime and sodium chloride. Feed also includes supplement, ready-mixed and mixed feedstuffs. These contain individual feedstuffs in a composition which ensures a balanced diet in respect of energy and protein supply and supply of vitamins, mineral salts and trace elements.

The concentration of the active compounds in the feed is usually about 0.01–500 ppm, preferably 0.1–50 ppm.

The active compounds can be added to the feed as such or in the form of premixes or feed concentrates.

An example of the composition of a chick-rearing feed containing 10 ppm of active compound according to the invention: 200 g of wheat, 340 g of corn, 361 g of shredded soy beans, 60 g of beef tallow, 15 g of dicalcium phosphate, 10 g of calcium carbonate, 4 g of iodinated sodium chloride, 7.5 g of vitamin-mineral mixture and 2.5 g of the active compound premix described below give, after thorough mixing, 1 kg of feed with an active compound content of 10 ppm.

One kg of vitamin-mineral mixture contains: 600 I.U. of vitamin A, 100 I.U. of vitamin $D_3$, 10 mg of vitamin E, 1 mg of vitamin $K_3$, 3 mg of riboflavin, 2 mg of pyridoxine, 20 mcg of vitamin $B_{12}$, 5 mg of calcium pantothenate, 30 mg of nicotinic acid, 200 mg of choline chloride, 200 mg of $MnSO_4 \times H_2O$, 140 mg of $ZnSO_4 \times 7 H_2O$, 100 mg of $FeSO_4 \times 7 H_2O$ and 20 mg of $CuSO_4 \times 5 H_2O$.

2.5 g of active compound premix contain, for example, 10 mg of active compound and 1 g of DL-methionine, the remainder being soy bean flour.

Example of the composition of a pig-rearing feed containing 8 ppm of active compound according to the invention: 630 g of shredded cereal feed (composed of 200 g of maize, 150 g of shredded barley, 150 g of shredded oats and 130 g of shredded wheat), 80 g of fish meal, 60 g of shredded soy beans, 60 g of tapioca flour, 38 g of brewers' yeast, 50 g of a vitamin-mineral mix for pigs, 30 g of linseed cake flour, 30 g of corn gluten feed, 10 g of soy bean oil, 10 g of sugarcane molasses and 2 g of active compound premix (composition, for example, as for the chick feed) give, after thorough mixing, 1 kg of feed with an active compound content of 8 ppm.

The feed mixtures described are intended for rearing and fattening preferably chicks and pigs, but they can also be used in the same or a similar composition for feeding other animals.

EXAMPLE A

Rat feeding experiment

Female laboratory rats weighing 150–165 g of the SPF Wistar type (breeder Hagemann) are fed ad libitum with standard rat food to which the desired amount of active compound is added. Each experimental set-up is performed with food of an identical batch, so that differences in the composition of the food cannot impair the comparability of the results.

The rats receive water ad libitum.

In each case 12 rats form one experimental group and are fed with food to which the desired amount of active compound is added. A control group is given food without active compound. The average body weight and the scatter in the body weights of the rats is the same in each experimental group, so that comparability of the experimental groups with one another is ensured.

The weight increase and food consumption are determined during the 13-day experiment and the relative weight increase in comparison with the untreated control is calculated. At the end of the experiment, the amount of perirenal fatty tissue is determined and calculated in comparison with the untreated control.

The results shown in the table are obtained:

| Rat feed experiment | | | |
|---|---|---|---|
| Active compound Example No. | Amount of active compound used ppm | Body weight increase (control = 00) | Amount of perireal fatty tissue (control = 100) |
| 1 | 25 | 188 | 69 |

EXAMPLE B

Pharmacological experiment with Beagle dogs to evaluate the tolerability (increase in heart rate)

To evaluate the effects of the active compounds according to the invention on the possible increase in heart rate, experiments are performed with conscious female Beagle dogs (10–15 kg body weight). The active compounds are administered orally in the desired amount, via a gelatine capsule, to the treatment group (3 animals) immediately after the morning feeding. The negative control group (3 animals) is given a placebo. The heart rate of the dogs is determined 50, 90 and 150 minutes after administration of the substance and is calculated in comparison with the untreated control group.

The results shown in the table are obtained.

TABLE 2

| Pharmacological experiment (increase in heart rate) on Beagle dogs | | | | |
|---|---|---|---|---|
| Active compound Example No. | Amount of active compound used (mg/kg of body weight) | Heart rate (beats/minute) Minutes after administration of the substance | | |
| | | 50 | 90 | 150 |
| untreated control | 0 | 72 | 72 | 63 |
| Example 1 | 0.075 | 113 | 113 | 80 |

Preparation Examples
Example 1

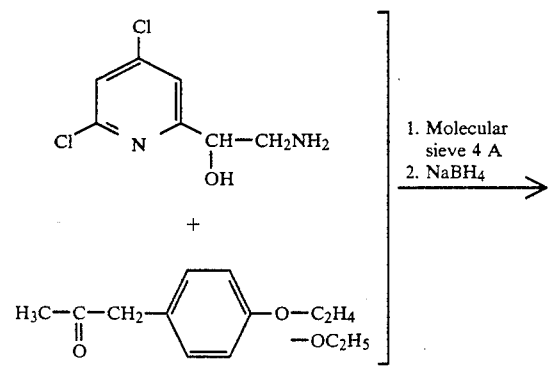

-continued
Preparation Examples
Example 1

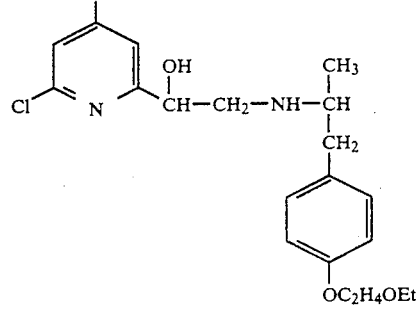

500 mg (2.42 mmol) of 2-amino-1-(2,4-dichloro-6-pyridyl)-ethanol, 536 mg (2.42 mmol) of 4-(2-ethoxyethoxy)pehnylacetone and 4.6 g of 3A molecular sieve are stirred in 100 ml of dry ethanol at room temperature for 48 hours. The mixture is then cooled to 0° C. and 389 mg (11 mmol) of NaBH4 are added. The mixture is stirred first at 0° C. for 30 minutes and then at room temperature for one hour. For working up, the mixture is filtered and the filtrate is evaporated in vacuo.

The residue is suspended in 100 ml of water and the suspension is acidified with concentrated HCl solution and extracted three times with $CH_2CL_2$. The extract is washed with dilute NaOH solution, dried with $Na_2SO_4$ and evaporated. For purification, the residue is chromotographed over silica gel using ethyl acetate/methanol. Yield: 690 mg of colorless oil, diastereomer mixture $^1$H-NMR(CDl$_3$) : 6.8–7.5 ppm (m 6H, H aromatic) 4.6 ppm (m, 1H,

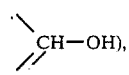

4.1 ppm (m, 2H, —CH$_2$—O), 3.8 ppm (m, 2H, —CH$_2$—)—), 3.6 ppm (δ, 2H, —O—CH$_2$—CH$_3$), 3.05–3.2 ppm (m, 1H, —CH—NH—), 2.7–2.9 ppm (m, 2H, —CH$_2$—NH—), 2.6 ppm (d, 2H, Ar-CH$_2$-CH), 1.25 ppm (t, 3H, CH$_2$—CH$_3$), 1.05 ppm (d, 3H, CH—CH$_3$)

4-(2Ethoxyethoxy)phenylacetone was prepared in accordance with the process described in DE-OS (German Published Specification) 2,034,277.

The following compounds were prepared analogously:

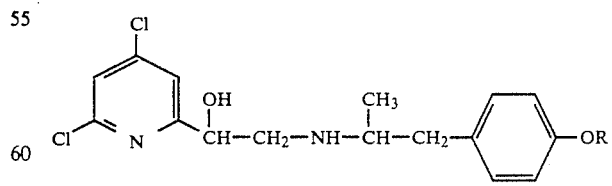

EXAMPLE 2

R= —H: yield: 413 mg of colorless oil, diastereomer mixture $^1$H-NMR (CDCl$_3$): 6.8–7.5 ppm (m, 6H, H aromatic), 4.6 ppm (m, 1H,

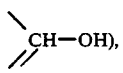

3.0-3.2 ppm (m, 1H, —CH—AR—CH$_2$—CH), 1.05 ppm (d, 4H, CH—CH$_3$).

EXAMPLE 3

R=—CH$_2$—CH$_2$OCH$_3$
Yield: 800 mg of colorless oil, diastereomer mixture
$^1$H-NMR(CKl$_3$): 6.8-7.5 ppm (m, 6H, H aromatic), 4.6 ppm (m, 1H,

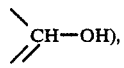

4.1 ppm (m, 2H, —CH$_2$—O—), 3.75 ppm (m, 2H, —CH$_2$—O—), 2.7-2.9 ppm (m, 2H, —CH$_2$—NH—), 2.6 ppm (d, 2H, Ar—CH$_2$—CH), 1.05 ppm (d, 3H, —CHCH$_3$)

EXAMPLE 4

R=—CH$_3$
Yield 760 mg of colorless oil, diastereomer mixture
H—NMR(CDl$_3$) 6.8-7.6 ppm (m, 6H, H aromatic), 4.6 ppm (m, 1H,

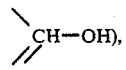

3.8 ppm (s, 3H, —OCH$_3$), 3.05-3.2 ppm (m, 1H, —CH—NH—), 2.7-2.9 ppm (m, 2H, —CH$_2$—NH—), 2.6 ppm (d, 2H, Ar—CH$_2$—CH), 1.05 ppm (d, 3H, CH—CH$_3$)

EXAMPLE 5

R=—CH$_2$—CH$_2$OH
Yield: 700 mg of colorless oil, diastereomer mixture
$^1$H—NMR(CDl$_3$) : 6.8-7.5 ppm (m, 6H, H aromatic) 4.6 ppm (m, 1H,

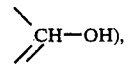

4.1 ppm (m, 2H, —CH$_2$—O—), 3.95 ppm (m, 2H, —CH$_2$—O—), 3.05-3.2 ppm (m, 1H, —CH—NH—), 2.7-2.9 ppm (m, 2H, —CH$_2$—NH—), 2.6 ppm (d, 2H, Ar—CH$_2$—CH), 1.05 ppm (d, 3H, —CH—CH$_3$) cl

PREPARATION OF THE STARTING COMPOUNDS

EXAMPLE 6

EXAMPLE FOR PROCESS 16

1-(2,4-Dichloro-6-pyridyl)-2-aminoethanol

A solution of 5.4 g (26.6 mmol) of (2,4-dichloro--b 6-pyridyl)-cyanohydrin in 60 ml of THF is added dropwise to 150 ml of a boiling 1 M solution of borane in THF. After 10 minutes, the mixture is acidified with 15 ml of concentrated hydrochloric acid, stirred for 15 minutes and then brought to pH 5 with dilute sodium hydroxide solution and the THF is evaporated off. After dilution with water, the mixture is washed twice with ethyl acetate, brought to pH 11 with dilute sodium hydroxide solution and extracted with ethyl acetate. After drying and evaporation, 3.8 g (70% of theory) of the title compound are obtained, melting point 117°-118° C.

EXAMPLE 7

EXAMPLE OF PROCESS 18

(2,4-Dichloro-6-pyridyl)-cyanohydrin 9.8 g of 40% strength aqueous NaHSO$_3$ solution are added to a solution of 4.8 g (27 mmol) of 2,4-dichloropyridine-6-aldehyde in 50 ml of ether. The mixture is diluted with 200 ml of water and 200 ml of ether and cooled to 10° C. and 3.7 g of NaCN are added. The batch is subsequently stirred for 5 minutes and the ether phase is separated off, dried over Na$_2$CO$_4$ and evaporated. The residue crystallizes completely under the oil pump. Colorless crystals, yield 5.4 g (99% of theory), melting point 56° C.

It is understood that the specification and examples are illustrative but not limitative of the present invention and that other embodiments within the spirit and scope of the invention will suggest themselves to those skilled in the art.

We claim:

1. A 2,4-dihalogeno-6-pyridyl-ethanolamine of the formula

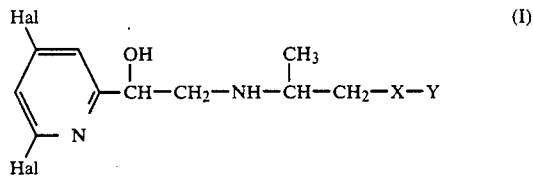

in which
Hal are identical or different and represent fluorine, chlorine or bromine,
X represents a direct bond of —CH$_2$— and
Y represents phenyl which is substituted by OH, C$_{1-4}$-alkoxy, C$_{1-4}$-alkoxy-C$_{1-4}$-alkoxy, carboxyl, aminocarbonyl, C$_{1-4}$-alkoxycarbonyl, hydroxy-C$_{1-4}$-alkoxy, amino-C$_{14}$-alkoxy, C$_{1-4}$-alkoxycarbonyl-C$_{1-4}$-alkoxy or phenyl-C$_1$-C$_4$-alkoxy,
or a physiologically tolerated salt or N-oxide thereof.
2. A 2,4-dihalogeno-6-pyridyl-ethanolamine according to claim 1, in which
X represents a direct bond, and
Y represents phenyl which is substituted by hydroxyl, methoxy, ethoxy, hydroxyethoxy, methoxyethoxy, ethoxyethoxy, methoxycarbonylmethoxy, ethoxycarbonylethoxy, phenylethyleneoxy or phenylpropyleneoxy.
3. A compound according to claim 1, in which
Hal represents chlorine,
X represents a direct bond, and
Y represents phenyl which is substituted in the 4-position by hydroxy, methoxy, ethoxy, hydroxyethoxy, methoxyethoxy, ethoxyethoxy, methoxycarbonylmethoxy or ethoxycarbonylethoxy.
4. A compound according to claim 1, wherein such compound is 2,3-dichloro-α-6-pyridinemethanol of the formula

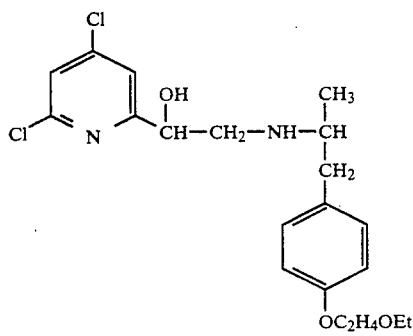

or a physiologically tolerated salt or N-oxide thereof.

5. A compound according to claim 1, wherein such compound is 2,3-dichloro-α-6-pyridinemethanol of the formula

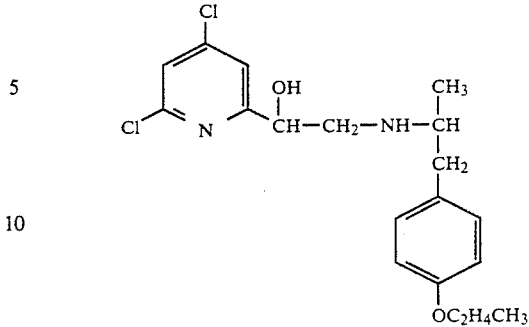

or a physiologically tolerated salt or N-oxide thereof.

6. A compound according to claim 1, wherein such compound is 2,3-dichloro-α-6-pyridinemethanol of the formula

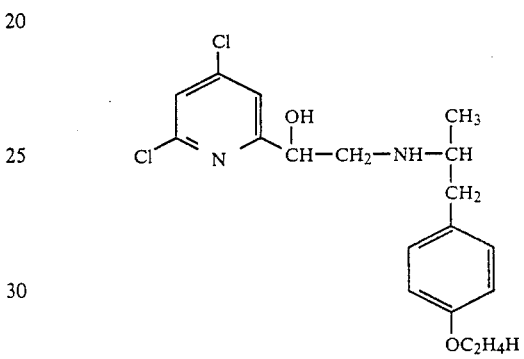

or a physiological tolerated salt or N-oxide thereof.

7. A composition for shifting the protein-fat ration of animals in favor of protein and for treating adiposity in humans and animals, comprising an effective amount of a 2,4-dihalogeno-6-pyridylethanolphenylisopropylamine according to claim 1, and an acceptable carrier.

8. A method for shifting the protein-fat ratio of animals in favor of protein and for treating adiposity in humans and animals, comprising administering to said animals or humans an amount effective therefor of a compound according to claim 1.

* * * * *

UNITED STATES PATENT AND TRADEMARK OFFICE
CERTIFICATE OF CORRECTION

PATENT NO. : 5,010,091

DATED : April 23, 1991

INVENTOR(S) : Lindel et al.

It is certified that error appears in the above-identified patent and that said Letters Patent is hereby corrected as shown below:

Col. 30, line 48    Delete " amino-$C_{14}$ " and substitute -- amino-$C_{1-4}$ --

Col. 30, line 67    After " dichloro-α - " insert -- [[[4-(2-ethoxyethoxy)phenethyl]-amino]methyl]--

Col. 31, line 40    After " dichloro -α- " insert -- [[[4-(2-methoxyethoxy)phenethyl]-amino]methyl] --

Col. 32, line 1-14  Delete " 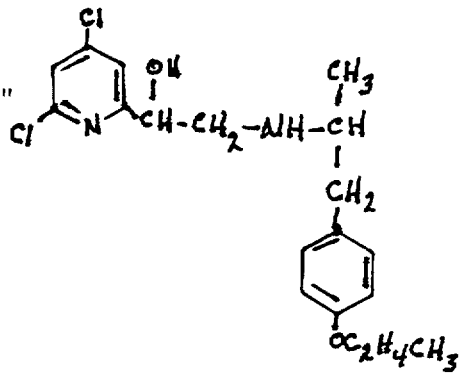 " and substitute -- 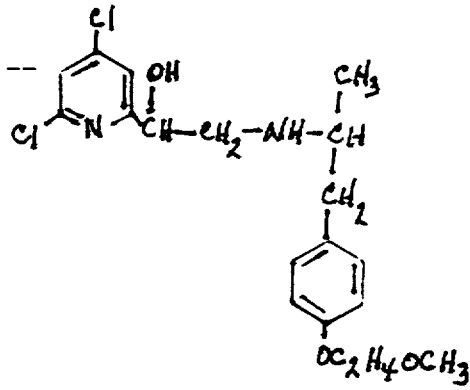 --

UNITED STATES PATENT AND TRADEMARK OFFICE
CERTIFICATE OF CORRECTION

PATENT NO. : 5,010,091

DATED : April 23, 1991

INVENTOR(S) : Lindel et al.

It is certified that error appears in the above-identified patent and that said Letters Patent is hereby corrected as shown below:

Col. 32, line 18    After " dichloro-α - " insert -- [[[4-(2-hydroxyethoxy) phenethyl]-amino]methyl] --

Col. 32, line 33    Delete " 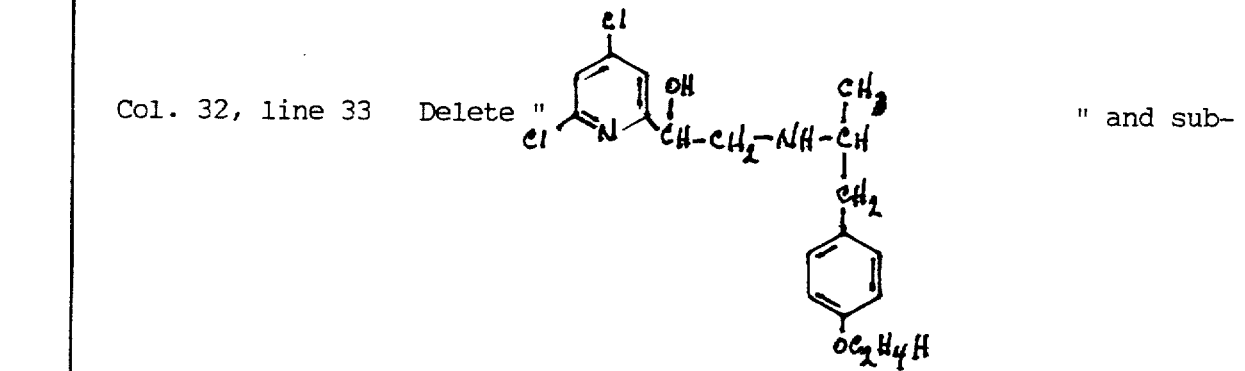 " and substitute -- 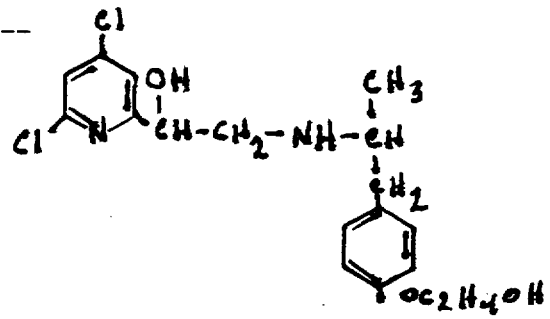 --

UNITED STATES PATENT AND TRADEMARK OFFICE
CERTIFICATE OF CORRECTION

PATENT NO. : 5,010,091
DATED : April 23, 1991
INVENTOR(S) : Lindel et al.

It is certified that error appears in the above-indentified patent and that said Letters Patent is hereby corrected as shown below:

Col. 32, line 35   Delete "ration" and substitute --ratio--.

Signed and Sealed this

Third Day of January, 1995

Attest:

BRUCE LEHMAN

*Attesting Officer*   *Commissioner of Patents and Trademarks*